United States Patent
Rombach et al.

(10) Patent No.: US 7,730,759 B2
(45) Date of Patent: Jun. 8, 2010

(54) METHOD AND DEVICE FOR CALIBRATING A HUMIDITY SENSOR AND SENSOR ARRANGEMENT HAVING HUMIDITY SENSOR CAPABLE OF CALIBRATION

(75) Inventors: Martin Rombach, Lenzkirch (DE); Markus Langenbacher, Lenzkirch (DE)

(73) Assignee: Testo AG, Lenzkirch (DE)

( * ) Notice: Subject to any disclaimer, the term of this patent is extended or adjusted under 35 U.S.C. 154(b) by 154 days.

(21) Appl. No.: 10/471,307

(22) PCT Filed: Jan. 3, 2003

(86) PCT No.: PCT/EP03/00033

§ 371 (c)(1),
(2), (4) Date: Sep. 9, 2003

(87) PCT Pub. No.: WO03/081231

PCT Pub. Date: Oct. 2, 2003

(65) Prior Publication Data

US 2004/0237625 A1 Dec. 2, 2004

(30) Foreign Application Priority Data

Jan. 30, 2002 (DE) .............................. 102 03 637

(51) Int. Cl.
*G01L 27/02* (2006.01)

(52) U.S. Cl. .......................... 73/1.59; 73/1.61; 73/1.62; 73/1.88

(58) Field of Classification Search ................. 73/1.01, 73/1.02, 1.06, 1.57, 1.59, 1.61, 1.62, 1.71, 73/1.88, 23.21, 29.01–29.03
See application file for complete search history.

(56) References Cited

U.S. PATENT DOCUMENTS

| | | | | |
|---|---|---|---|---|
| 3,532,270 | A | | 10/1970 | Schoen, Jr. ................. 236/44 R |
| 5,033,284 | A | * | 7/1991 | Belt et al. ..................... 73/1.06 |
| 5,343,747 | A | * | 9/1994 | Rosen ...................... 73/335.06 |
| 5,502,659 | A | | 3/1996 | Braster et al. ............... 702/104 |
| 5,792,938 | A | * | 8/1998 | Gokhfeld ................... 73/29.02 |
| 6,073,480 | A | | 6/2000 | Gokhfeld ................... 73/29.02 |
| 6,299,147 | B1 | | 10/2001 | Mitter ......................... 291/128 |

OTHER PUBLICATIONS

Hardy, Bob, "Relative Humidity Uncertainty Analysis of the Thunder Scientific Model 2500 Two Pressure Humidity Generator", Thunder Scientific Corp., 1998, pp. 1-13.*
"Model 2500 Benchtop/Mobile Two Pressure Humidity Generator", Thunder Scientific Corp., pp. 1-4.*

(Continued)

*Primary Examiner*—David A. Rogers
(74) *Attorney, Agent, or Firm*—Muirhead and Saturnelli, LLC

(57) ABSTRACT

For calibrating a humidity sensor, the latter is used to measure the relative humidity ($U_1$, $U_2$) at each of two known gas pressure values ($P_1$, $P_2$), likewise to be measured if necessary. At the same time, other ambient conditions are kept constant. A correction value for correction of the measured values of the humidity sensor to be subtracted from the latter is then obtained from the formula: $k = ((P_1/P_2)*U_2 - U_1)/(P_1/P_2 - 1)$. The humidity sensor is thus capable of calibration without measurement of the actual humidity value.

15 Claims, 2 Drawing Sheets

OTHER PUBLICATIONS

Kester, Walt, "Practical Design Techniques for Sensor Signal Conditioning", 1999, Analog Devices, Inc., pp. 1.1-2.19.*

Cubberly, William H., "SAE Dictionary of Aerospace Engineering", 1992, Society of Automotive Engineers, pp. 106-107.*

"Relative Humidity Question", Internet email corresponance from Dr. Steve Ackerman, Professor of Atmospheric and Ocean Sciences at the University of Wisconsin-Madison.*

* cited by examiner

METHOD AND DEVICE FOR CALIBRATING A HUMIDITY SENSOR AND SENSOR ARRANGEMENT HAVING HUMIDITY SENSOR CAPABLE OF CALIBRATION

BACKGROUND OF THE INVENTION

1. Technical Field

The present invention relates to a method of calibrating a humidity sensor.

2. Description of the Related Art

Humidity sensors are used to measure the relative humidity in open or closed volumes of gas, i.e., the quantity of humidity that is dissolved in the particular gas relative to the maximum quantity of humidity soluble in the gas at the given temperature.

Such measurements are familiar to, for example, the average consumer as measurements of relative atmospheric humidity for the determination of climatic conditions, but they are also common in the industrial field for determination of, for example, the relative atmospheric humidity in gas vessels under pressure.

Humidity sensors are often severely stressed by physical and chemical influences and their response characteristic may thereby be significantly altered with respect to the initial calibration. Recalibration is therefore necessary at certain intervals.

The related art (German Patent Application 3936138 A1, U.S. Pat. No. 6,073,480) includes calibration of a humidity sensor in that a first humidity measurement is carried out at a first temperature and then a second humidity measurement is carried out at a second temperature, the gas pressure remaining the same in both measurements. The measured temperature and humidity values permit computation of a correction value for the humidity measurement, since the mathematical relationship between temperature and actual relative humidity is known.

However, for the use of this technique it is necessary to place temperature sensors in the region of the humidity sensors, as well as to provide heating or cooling elements. In addition, such a method of calibration requires time for setting the particular measurement temperatures.

The physical and chemical influences result in a change or a drift in the characteristic curve of the sensor. The change results in an offset but not in a change of the slope of the characteristic curve. This is particularly true for small values of humidity, e.g., humidity values below 15 percent, and which is important when, for example, monitoring the remaining humidity in compressed air.

Accordingly, it would be desirable to provide a method of recalibrating a humidity sensor, which had initially been calibrated and then changed its characteristic curve due to physical and chemical influences during its operation, and a corresponding device. It may also be desirable to provide a sensor arrangement having a calibratable humidity sensor of the type mentioned at the beginning, wherein the calibration procedure is simplified and as few as possible auxiliary means are required for its performance.

SUMMARY OF THE INVENTION

According to the present invention, at a first pressure P1 and at a second pressure P2 different from the first and at otherwise like conditions, humidity values U1, U2 are detected in each instance, at least the ratio of first pressure value P1 and second pressure value P2 being known, and in that the correction value for the humidity sensor is determined from the ratio of the pressure values and the measured humidity values.

According further to the present invention, a device has a pressure sensor, an input means for input of the measured values of the humidity sensor into a first data memory and a computing means that determines a correction value of the humidity sensor from the ratio of two pressure values and two humidity values detected at the particular pressure values under otherwise like conditions.

If the humidity values are measured at two unlike pressures, the temperature and other ambient conditions being kept constant and the same quantity of absolute humidity remaining dissolved in the gas, the value of the relative humidity between the two measurements varies. The ratio of the two actually existing humidity values of the relative gas humidity may be inferred from the ratio of the two pressure values. If the ratios of the pressures and the measured relative gas humidity values do not agree, the correction value that is to be applied to the particular humidity measurement may be determined from the difference. This correction value is then to be subtracted from or added to the measured value of the relative humidity.

The device for calibrating a humidity sensor accordingly has a pressure sensor, if the latter is not already provided in the system in the region of the humidity sensor, as well as an input means via which the measured humidity values of the humidity sensor may be supplied to the calibrating device. A computing means of the calibrating device then determines the correction value from the measured data and outputs it.

The method of calibration advantageously is carried out in that offset k to be subtracted from a measured humidity value is determined according to the equation:

$$k = \frac{(P1/P2) * U2 - U1}{(P1/(P2-1))}$$

Ideally, for a gas of constant consistency and constant temperature, the ratio of the two pressure values at which the measurement is made corresponds to the ratio of the actually existing relative humidity values:

$$\frac{P1}{P2} = \frac{U1(\text{actual})}{U2(\text{actual})}$$

Since the measured humidity values U1, U2 do not agree with the actual humidity values before calibration, the actual humidity value $$U1(\text{actual}) = U1 - k \text{ and } U2(\text{actual}) = U2 - k$$

is computed.

The equation:

$$\frac{P1}{P2} = \frac{(U1-k)}{(U2-k)}$$

is obtained.

Solved for k, this equation gives:

$$k = \frac{(P1/P2) * U2 - U1}{(P1/(P2-1))}$$

This applies on the assumption that k is independent of the value of U. The calibration method according to the present invention thus permits the humidity sensor to be calibrated with the use of a pressure sensor without the actually existing humidity being directly determined. It is only necessary to use a calibrated pressure sensor, which, however, is simple in that pressure sensors are relatively stable in their calibration.

In practice, the method of calibrating a humidity sensor in a pressurizable gas-filled system is advantageously carried out in that gas is discharged or supplied by a valve provided in the system, and in that pressure values and humidity values are recorded before and after the discharge/supply of gas, temperature equalization being awaited before each humidity measurement.

Pressurizable gas-filled systems typically are already provided with valves for filling with gas or for discharging gas. Gas may be discharged or supplied via such a valve, and discharged gas may be stored in an external pressure tank. Humidity measurements are made each time before and after discharge and supply of gas, and temperature equalization must be awaited after discharge or supply of gas, since both humidity measurements must take place at the same temperature and since, owing to expansion of the gas and owing to pressure increase, a temperature reduction or increase is to be awaited. Instead of valves, pressure reducers may alternatively be used.

For calibrating the humidity sensor, the latter may be operated in a small, pressure-tight closed part (measuring chamber) of the system, so that the different pressure values do not require a pressure modification in the entire system, but only the gas pressure in the partial volume in which the humidity sensor is located need be varied. The corresponding pressure sensors may already be provided in the system in the region of the humidity sensor, but they may alternatively also be introduced into the volume in the course of calibration or the particular pressure may be measured outside the system upon discharge or supply of gas in the respective feed line. Hence calibration may be carried out simply, reliably and rapidly by service personnel, with no major changes or installations in the pressurizable gas-filled system. The measuring chamber having a built-in humidity sensor is thus designed to produce, by suitable means (valve, pressure reducer, etc.), the two pressures for the humidity sensor required for the calibration method.

The present invention in addition relates to a sensor arrangement having a humidity sensor capable of calibration according to the method set forth herein and having a correction means with a memory, in which a correction value to be subtracted from the measured humidity value is storable, the correction means subtracting the correction value from the detected measured value of the humidity and in particular delivering the result to a display means.

The sensor arrangement thus has a correction means by which, after a calibration, the humidity value detected by the humidity sensor is corrected by the correction value, so that the actually existing humidity value is available as a corrected measured value for reading off or for further processing in, for example, a control room.

The present invention is shown below by way of example in the drawing and is then explained.

DETAILED DESCRIPTION OF VARIOUS EMBODIMENTS

Figure 1:
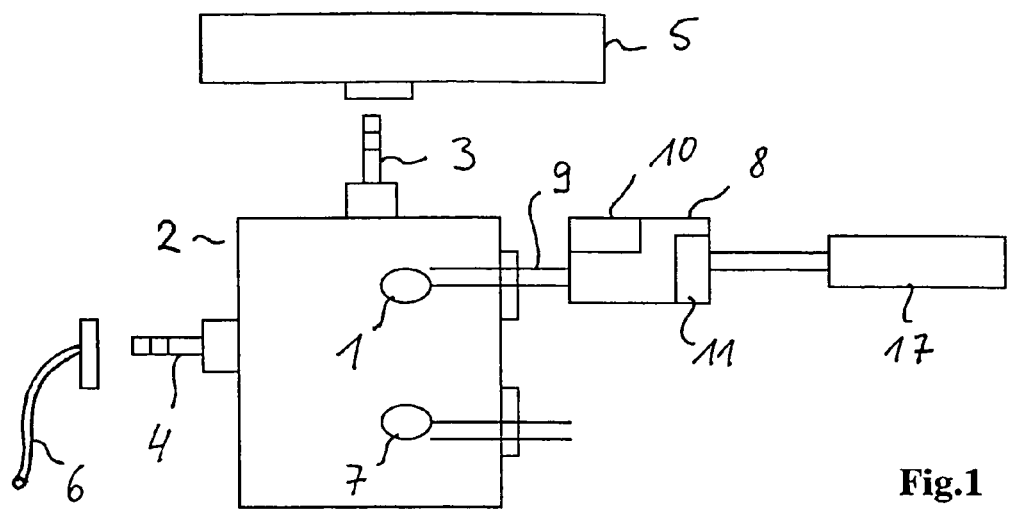
FIG. 1 in a schematic representation shows a humidity sensor and a device for its calibration, FIG. 2 schematically shows the function of the computing means for determination of the correction value.

FIG. 1 shows a humidity sensor 1 in a gas-tight measuring chamber 2. Measuring chamber 2 has a first gas connection 3 and a second gas connection 4, by which the measuring chamber may be connected to a gas-filled pressurizable system 5 and to an additional gas chamber by a pressure hose 6.

A pressure sensor 7 is additionally provided in measuring chamber 2. This pressure sensor may be a conventional pressure sensor, but it should be calibrated and have a measurement accuracy that is as high as possible.

In order to measure, for example, the humidity in pressurizable system 5 and at the same time calibrate humidity sensor 1, measuring chamber 2 is first connected via first gas connection 3 to pressurizable system 5, so that gas exchange and pressure equalization may take place. Then the gas pressure in the measuring chamber is measured by pressure sensor 7 and measuring chamber 2 is separated from the pressurizable system. In addition, under the conditions now existing, the first humidity value is measured by humidity sensor 1. At the same time, correction means 8, which is connected to feed communication 9 of the humidity sensor, and which in normal operation subtracts the correction value stored in memory 10 from the direct measured value of humidity sensor 1, is bypassed for calibration.

A fixed quantity of gas is then discharged from measuring chamber 2 by second gas connection 4 via pressure hose 6, so that the gas pressure is reduced. Then measuring chamber 2 is again closed gas-tight.

After the temperature in measuring chamber 2 has returned to normal, a second humidity value U2 and a second pressure value P2 are measured. From the two measured pressure values and the two measured and uncorrected humidity measurement values a correction value may then be determined, which is stored in memory 10. On subsequent humidity measurements within correction means 8 the correction value stored in the memory is then subtracted from the humidity value measured by humidity sensor 1 in a subtraction unit 11 and output as the corrected measured value by a display 17.

Figure 2:
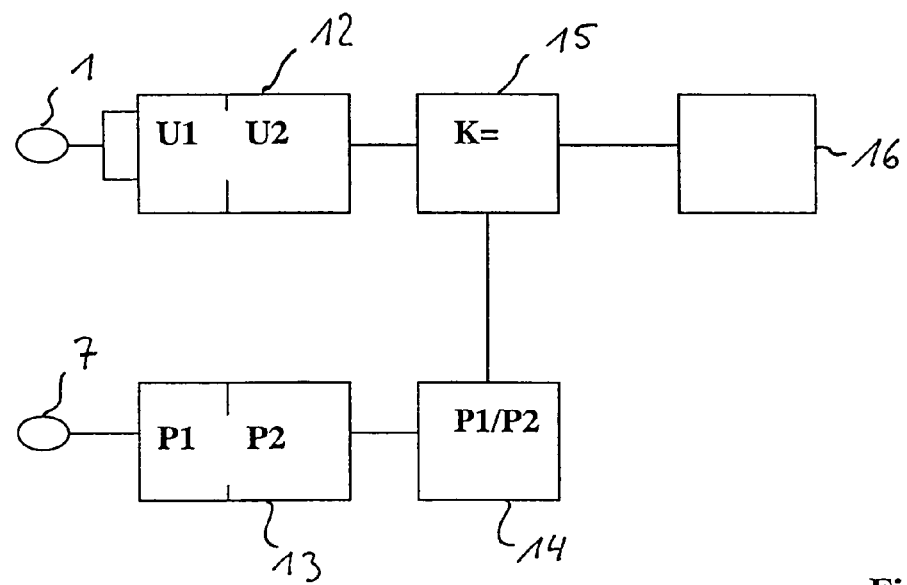

The detection and computation steps in a calibration procedure are represented schematically in FIG. 2. In a first step, humidity value U1 is detected by humidity sensor 1. At the same time, pressure value P1 is detected by pressure sensor 7. The two measured values are stored in a first data memory 12 and a second data memory 13.

In a second step, at reduced pressure and otherwise like ambient conditions, a second humidity value U2 and a second pressure value P2 are measured. The two measured values are again stored in corresponding first and second data memories 12, 13.

Then the P1/P2 ratio is computed and stored in a third data memory 14. In a computing means 15, k is computed by a microprocessor according to the formula given in as shown above and sent on to an output means 16, which sends the correction value on to, for example, correction means 8, where it is stored in memory 10.

Figure 3:
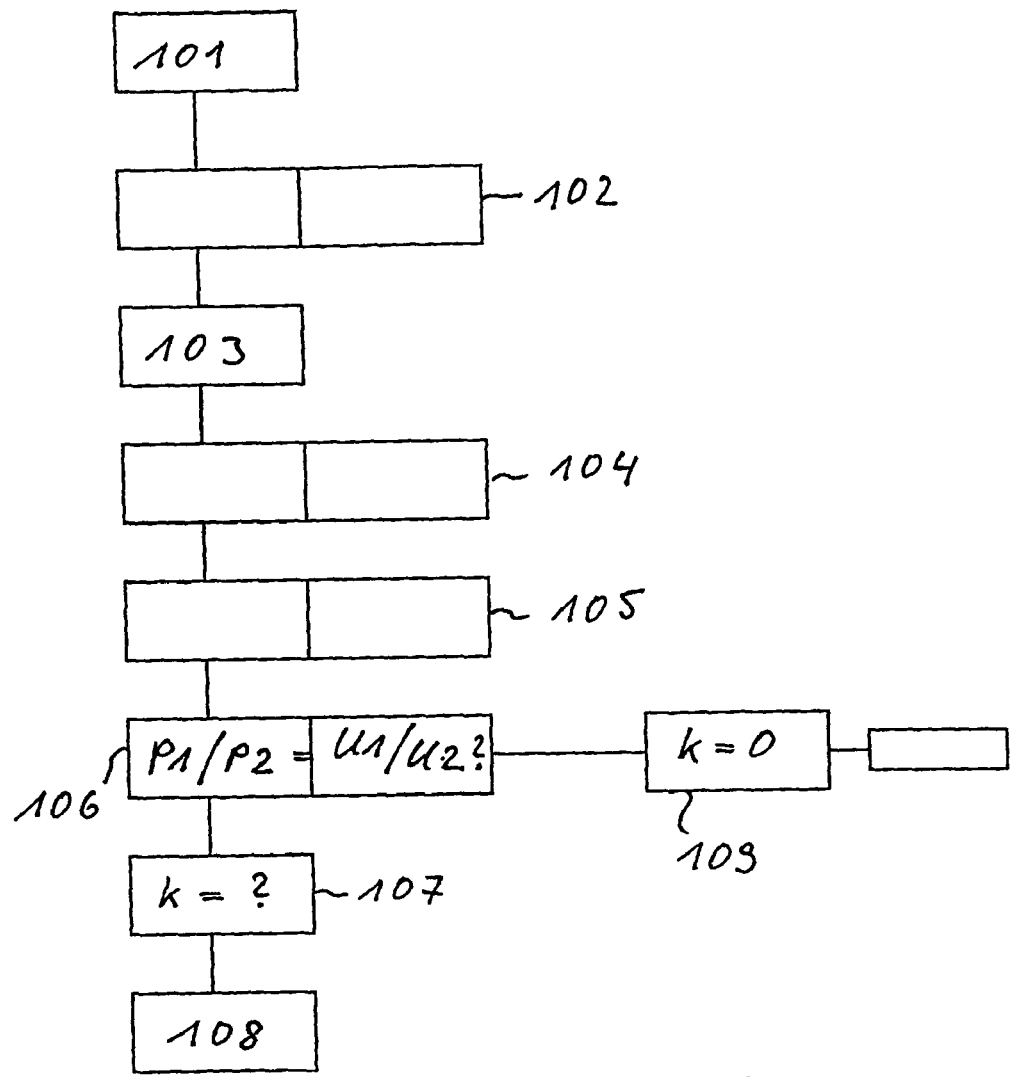
FIG. 3 shows a flow diagram of the calibration procedure.

In FIG. 3 the calibration procedure is again represented in the form of sequential steps. In a first step 101, a specified pressure is set in the measuring chamber. In second step 102, pressure value P1 and humidity value U1 are measured. In third step 103, the pressure in the measuring chamber is varied by, for example, discharging gas. In fourth step 104, a second pressure P2 and a second humidity value U2 are measured. In fifth step 105, the quotient of P1 and P2 and the quotient of U1 and U2 are computed. In sixth step 106, the quotients of P1 and P2 and of U1 and U2 are compared with one another. If the two quotients agree, in the next step (109) the correction value k=0 is set and the calibration procedure ended. If the quotients fail to agree, in next step 107 k is computed from the formula as shown above. In eighth step 108, k is then stored in memory 10 for correction of subsequent humidity measurements.

In an exemplary calibration, a first pressure value P1=4.5 bar was measured initially. At this pressure value a humidity value U1=1.7% relative humidity was measured by the humidity sensor. At a second gas pressure, pressure value P2=0.9 bar and a humidity value of 0.5% relative humidity were measured. The value of 5 was obtained as the quotient of the pressure values. Hence the relative humidity value at a high pressure of 1.7% relative humidity would have to drop to 0.34% relative humidity at the lower pressure value. However, a value of 0.5% relative humidity was measured at the lower pressure value. In other words, a correction is necessary, k being obtained as follows:

$$k = \frac{5*(0.5\% \text{ rel.humidity} - 1.7\% \text{ rel.humidity})}{5-1} = 0.2\% \text{ rel.humidity}$$

Then the corrected humidity values according to the measurement carried out are U1 (actual)=1.7% rel.humidity−0.2% rel.humidity=1.5% rel.humidity and U2(actual)=0.5% rel.humidity−0.2% rel.humidity=0.3% rel.humidity The calibration method described may be performed cyclically or periodically during operation of the humidity sensor and a new correction value computed and stored each time.

The method according to the present invention may be implemented in a variety of ways in addition to the embodiments shown. In particular, there are numerous embodiments of devices for performing the method according to the present invention.

What is claimed is:

1. A method of calibrating a humidity sensor, comprising:
   measuring a first pressure using a calibrated pressure sensor;
   measuring a first humidity value;
   measuring a second pressure using the calibrated pressure sensor;
   measuring a second humidity value;
   determining a correction value according to the first and second pressures and the first and second humidity values, and at otherwise like conditions; and
   maintaining the correction value to be applied to humidity measurements of the humidity sensor.

2. The method of claim 1, wherein determining the correction value includes using the equation:

$k=((P1/P2)*U2-U1)/P1/P2-1)$, where k is the correction value, P1 is the first pressure, P2 is the second pressure, U1 is the first humidity value, and U2 is the second humidity value.

3. The method of claim 1, wherein the first humidity value and the first pressure are measured at a first time and wherein the second humidity value and second pressure are measured at a second time different from the first time.

4. The method of claim 1, wherein the second pressure is measured after the first pressure is measured and wherein the second pressure is less than the first pressure.

5. The method of claim 1, further comprising:
   storing the correction value in a memory location that is accessed when the correction value is being applied to humidity measurements of the humidity sensor.

6. The method of claim 1, wherein the correction value is subtracted from humidity measurements of the humidity sensor.

7. A method of calibrating a humidity sensor, in which a humidity value is in each instance detected by the humidity sensor under first ambient conditions and under second ambient conditions different from the first, and in which a correction value for the humidity sensor is determined from the parameters of the ambient conditions and the measured humidity values,
   wherein, at a first pressure and at a second pressure different from the first that are determined using a calibrated pressure sensor, and at otherwise like conditions, a humidity value is detected in each instance, at least the ratio of the first pressure value and the second pressure value being known; and the correction value for the humidity sensor is determined from the ratio of the pressure values and the measured humidity values.

8. The method as recited in claim 7,
   wherein gas is discharged or supplied by a valve provided in the system; and pressure values and humidity values are recorded before and after the discharge/supply of gas, temperature equalization being awaited before each humidity measurement.

9. The method as recited in claim 7,
   wherein a correction factor k to be subtracted from a measured humidity value is determined according to the equation:

$k=((P1/P2)*U2-U1)/(P1/P2-1)$.

10. The method as recited in claim 9,
    wherein gas is discharged or supplied by a valve provided in the system; and pressure values and humidity values are recorded before and after the discharge/supply of gas, temperature equalization being awaited before each humidity measurement.

11. A humidity sensor, comprising:
    a memory containing a correction value that is determined according to calibrated first and second pressure measurements and first and second humidity value measurements measured respectively at the first and second pressures and at otherwise like conditions; and
    a microprocessor that applies the correction value to the first and second humidity value measurements of the humidity sensor.

12. The humidity sensor of claim 11, wherein the correction value is determined according to the equation:

$k=((P1/P2)*U2-U1)/(P1/P2-1)$, where k is the correction value, P1 is the first pressure, P2 is the second pressure, U1 is the first humidity value, and U2 is the second humidity value.

13. The humidity sensor of claim 11, wherein the microprocessor subtracts the correction value from humidity measurements of the humidity sensor.

14. A device for calibrating a humidity sensor, comprising:
a calibrated pressure sensor;
a first data memory that stores measured values of the humidity sensor; and
a microprocessor that determines a correction value of the humidity sensor from the ratio of two pressure values measured by the calibrated pressure sensor and two humidity values detected at the particular pressure values under otherwise like conditions.

15. A sensor arrangement, comprising:
a humidity sensor;
a memory in which a correction value to be subtracted from a measured humidity value is stored; and
a microprocessor coupled to the memory, the microprocessor subtracting the correction value from the detected measured value of the humidity and delivering the result to a display, wherein the correction value is determined using known and calibrated first and second pressures and a first measured humidity value measured at the first pressure and a second measured humidity value measured at the second pressures and under otherwise like conditions.

* * * * *